US008506560B2

(12) United States Patent
McBride, Jr. et al.

(10) Patent No.: US 8,506,560 B2
(45) Date of Patent: Aug. 13, 2013

(54) CONTAINER FOR STORING A CRYOSURGERY DEVICE

(75) Inventors: Robert T. McBride, Jr., Cleveland, TN (US); Sergio Gedanke, Brooklyn, NY (US); Wing-Kwong Keung, Perrysburg, OH (US); Leonora M. Brozell, Maumee, OH (US)

(73) Assignee: MSD Consumer Care, Inc., Memphis, TN (US)

( * ) Notice: Subject to any disclaimer, the term of this patent is extended or adjusted under 35 U.S.C. 154(b) by 891 days.

(21) Appl. No.: 12/332,864

(22) Filed: Dec. 11, 2008

(65) Prior Publication Data
US 2009/0234346 A1    Sep. 17, 2009

Related U.S. Application Data

(60) Provisional application No. 61/013,781, filed on Dec. 14, 2007.

(51) Int. Cl.
*A61B 18/02* (2006.01)

(52) U.S. Cl.
USPC ............................. 606/25; 606/26

(58) Field of Classification Search
USPC .................. 606/22, 23, 25, 26; D3/294, 295, D3/203.1, 313, 315, 316; 206/570, 572
See application file for complete search history.

(56) References Cited

U.S. PATENT DOCUMENTS

| | | | |
|---|---|---|---|
| 4,072,152 A | 2/1978 | Linehan | |
| 4,116,199 A | 9/1978 | Bryne | |
| 4,293,074 A * | 10/1981 | Dunsky | 206/572 |
| 4,313,306 A | 2/1982 | Torre | |
| 5,098,428 A | 3/1992 | Sandlin et al. | |
| 5,449,071 A * | 9/1995 | Levy | 206/569 |
| D379,562 S * | 6/1997 | Carter | D3/295 |
| 6,254,294 B1 * | 7/2001 | Muhar | 401/26 |
| 2006/0189968 A1* | 8/2006 | Howlett et al. | 606/25 |
| 2008/0208183 A1* | 8/2008 | Marin et al. | 606/22 |

FOREIGN PATENT DOCUMENTS

JP   56-91745    7/1981
WO   WO 2006114532 A1 * 11/2006

OTHER PUBLICATIONS

International Search Report for PCT/US2007/020475 mailed Mar. 3, 2009, Cossio Rodriguez.
ROC (Taiwan) Search Report for patent Application No. 097148309 dated Nov. 9, 2011.

* cited by examiner

*Primary Examiner* — Laura Bouchelle
(74) *Attorney, Agent, or Firm* — Dianne Pecoraro; Matthew J. Golden; Catherine D. Fitch (57) ABSTRACT

A container for a cryosurgery device which includes a cryogen bottle. The container includes a container body including an internal space sufficiently large to hold the cryogen bottle; a valve actuation assembly mechanically coupled to the container body, the valve actuation assembly configured to actuate a valve on the cryogen bottle; and a reservoir positioned relative to the valve actuation assembly so that the reservoir receives cryogen from the cryogen bottle when the valve on the cryogen bottle is actuated using the valve actuation assembly.

19 Claims, 14 Drawing Sheets

CONTAINER FOR STORING A CRYOSURGERY DEVICE

RELATED APPLICATION

This application claims priority to 61/013,781 Dec. 14, 2007 and is generally related to U.S. application Ser. No. 11/222,353, entitled "Cryosurgery Device," filed Sep. 8, 2005 now U.S. Pat. No. 7,604,632.

FIELD OF THE INVENTION

Some example embodiments of present invention include a container configured to store a cryosurgery device and a cryosurgery kit.

BACKGROUND

Cryosurgery devices are used for removing skin lesions such as warts. These devices have traditionally utilized liquid nitrogen as a medium for cooling down the tissue of a skin lesion to a temperature necessary to destroy the tissue. However, since liquid nitrogen has a boiling point of −196° C. and is therefore difficult to handle and administer safely, cryosurgery devices employing a pressurized liquid refrigerant having a higher boiling point, e.g. −20° C. to −50° C., have recently been developed and are now available for over-the-counter consumer use.

These more recent cryosurgery devices typically employ an aerosol container, whose liquid refrigerant is directed through a conduit to a porous tip. The tip is then applied to the skin lesion for a prescribed period of time. However, the manner in which the refrigerant is transferred from the aerosol container to the tip may not sufficiently limit the loss of the refrigerant during such transfer and may not sufficiently prevent accidental release of the refrigerant.

DETAILED DESCRIPTION OF EXAMPLE EMBODIMENTS

The inventors of the present application have recognized that there is a need for a cryosurgery device container that efficiently stores parts belonging to a cryosurgery device and also provides for safe and efficient use of the device.

One example embodiment of the present invention is a cryosurgery device container which includes a base having compartments for storing all of the parts of a cryosurgery device, such as a cryogen bottle and applicator tips, as well as operating instructions. In addition, a cryogen bottle valve actuator and reservoir are integrated into the base. The container also includes a transparent door for the applicator tips and a transparent cover that fits on the base. The container has several advantages. First of all, a cryogen bottle valve actuator and reservoir integrated into a stable base allow the bottle to be actuated in a simple manner—with one hand, if need be—and allow refrigerant from the cryogen bottle to be stored safely and conveniently during use, without leakage or spillage. In addition, the transparent lid allows all of the device parts to be held in place and enables one to see all the device parts with the lid on the base. Furthermore, the compartment for the cryogen bottle is oriented in the base in such a manner, that the cryogen bottle is tilted back slightly and any logo or other information on the bottle is more visible to a customer in a store.

Another example embodiment of the present invention is a cryosurgery kit which may include the above-mentioned container, e.g., the base and transparent cover, and also the above-mentioned items belonging to or associated with a cryosurgery device, e.g., a cryogen bottle, integrated valve actuator/reservoir, applicator tips, and operating instructions.

Another example embodiment of the present invention is a container for a cryosurgery device which includes a cryogen bottle. The example container has a container body including an internal space sufficiently large to hold the cryogen bottle; a valve actuation assembly mechanically coupled to the container body, the valve actuation assembly configured to actuate a valve on the cryogen bottle; and a reservoir positioned relative to the valve actuation assembly so that the reservoir receives refrigerant from the cryogen bottle when the valve on the cryogen bottle is actuated using the valve actuation assembly.

Some other example embodiments include a cryosurgery kit having a cryogen bottle; a container holding the cryogen bottle; and a valve actuation assembly mechanically coupled to the container, the valve actuation assembly configured to actuate a valve on the cryogen bottle.

In another example embodiment of the present invention, a container for a cryosurgery device that includes a cryogen bottle includes a container body containing an internal space sufficiently large to hold the cryogen bottle; a valve actuation assembly mechanically coupled to the container body, the valve actuation assembly configured to actuate a valve on the cryogen bottle; a reservoir positioned relative to the valve actuation assembly so that the reservoir receives refrigerant from the cryogen bottle when the valve on the cryogen bottle is actuated using the valve actuation assembly; a base, wherein the valve actuation assembly and the reservoir are integral parts of the base; and a cover configured to form a closed volume with the base, the closed volume dimensioned large enough to contain the cryogen bottle; wherein the reservoir is situated beneath the valve actuation assembly; the base includes a first depression into which the cryogen bottle may be placed; the first depression is approximately frustoconical; the first depression has an approximately circular bottom and is oriented such that when the cryogen bottle is placed in the first depression, the cryogen bottle is tilted back from a vertical position; the base includes a second depression in which applicator tips may be stored; the second depression has approximately a shape of a rectangular prism; the base includes a door that closes off the second depression when the door is in a closed position; the cover is substantially transparent; the base includes a third depression contiguous with the second depression; the third depression has approximately a shape of an arch; and the base includes a fourth depression having a shape of an oblong slot.

Additional example embodiments include a cryosurgery kit that has a cryogen bottle; a container holding the cryogen bottle; a valve actuation assembly mechanically coupled to the container, the valve actuation assembly configured to actuate a valve on the cryogen bottle; a liquid storage reservoir coupled to the container, the reservoir positioned relative to the valve actuation assembly so that the reservoir receives refrigerant from the cryogen bottle when the valve on the cryogen bottle is actuated using the valve actuation assembly; a transparent cover coupled to the base; a plurality of applicator tips; and an information booklet; wherein the container further comprises a base; the valve actuation assembly is an integral part of the base; the reservoir is an integral part of the base; the base includes a frustoconical-shaped depression, a rectangular-prism shaped depression having a substantially transparent door, and a slot-shaped depression; the cryogen bottle is situated in the frustoconical-shaped depression; the plurality of applicator tips are situated in the rectangular-shaped depression; and the information booklet is situated in the slot-shaped depression.

Other features and aspects of the present invention will become more fully apparent from the following detailed description of some example embodiments, the appended claims and the accompanying drawings.

Figure 1:
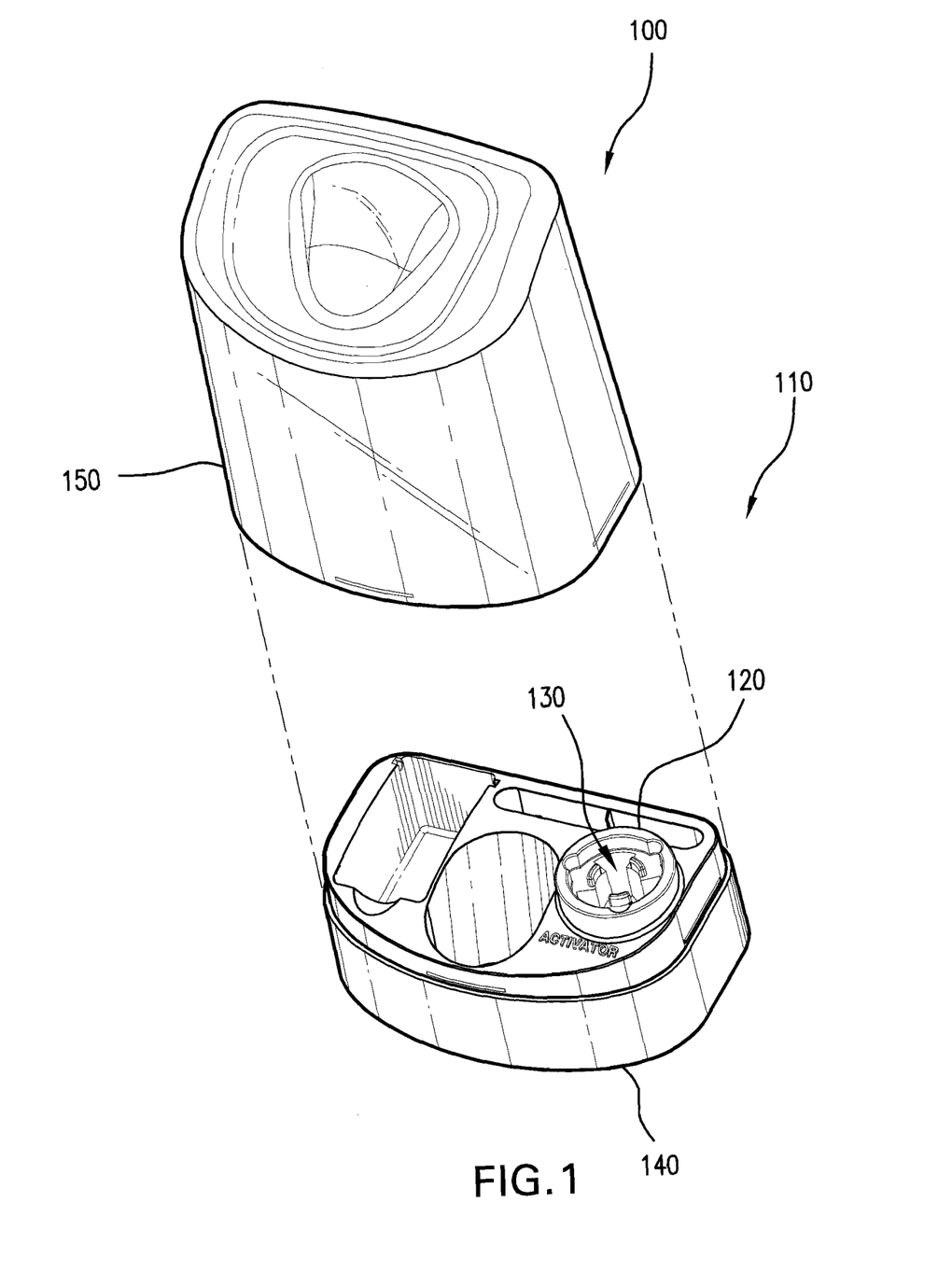
FIG. 1 is an exploded view of an example container for a cryosurgery device, according to an example embodiment of the present invention.

FIG. 1 is a perspective view of an example container for a cryosurgery device, according to an example embodiment of the present invention. The container 100 may include a container body 110 for storing a cryogen bottle 200 (see FIG. 8). The container 100 may also include a valve actuation assembly 120 mechanically coupled to the container body 110. A preferred method of mechanically coupling the valve actuation assembly to the container body 110 is integral molding, but adhesive bonding, friction-fitting, screws, etc., may also be employed. The valve actuation assembly 120 may be configured to actuate a valve 230 (see FIG. 9) of the cryogen bottle 200 and allow at least some of a refrigerant contained in the cryogen bottle 200 to be released. The valve actuation assembly 120 may be designed so as to only be able to mate with the cryogen bottle 200 and actuate the valve 230 at specific angular positions of the bottle 200, thereby reducing the chances of accidental release of refrigerant. In the example embodiments discussed with regard to FIGS. 9 and 10, this is accomplished by providing arcuate keys 124 on the valve actuation assembly 120 that mate with slots 240 provided on the cryogen bottle 200. However, other ways of limiting actuation of valve 230 are possible. Further with respect to FIG. 1, the container 100 may additionally include a reservoir 130 configured to hold at least some liquid refrigerant expelled from the cryogen bottle 200, after the valve 230 of the cryogen bottle 200 has been actuated via the valve actuation assembly 120. The container 100 may also include a base 140 and a cover 150.

Figure 2:
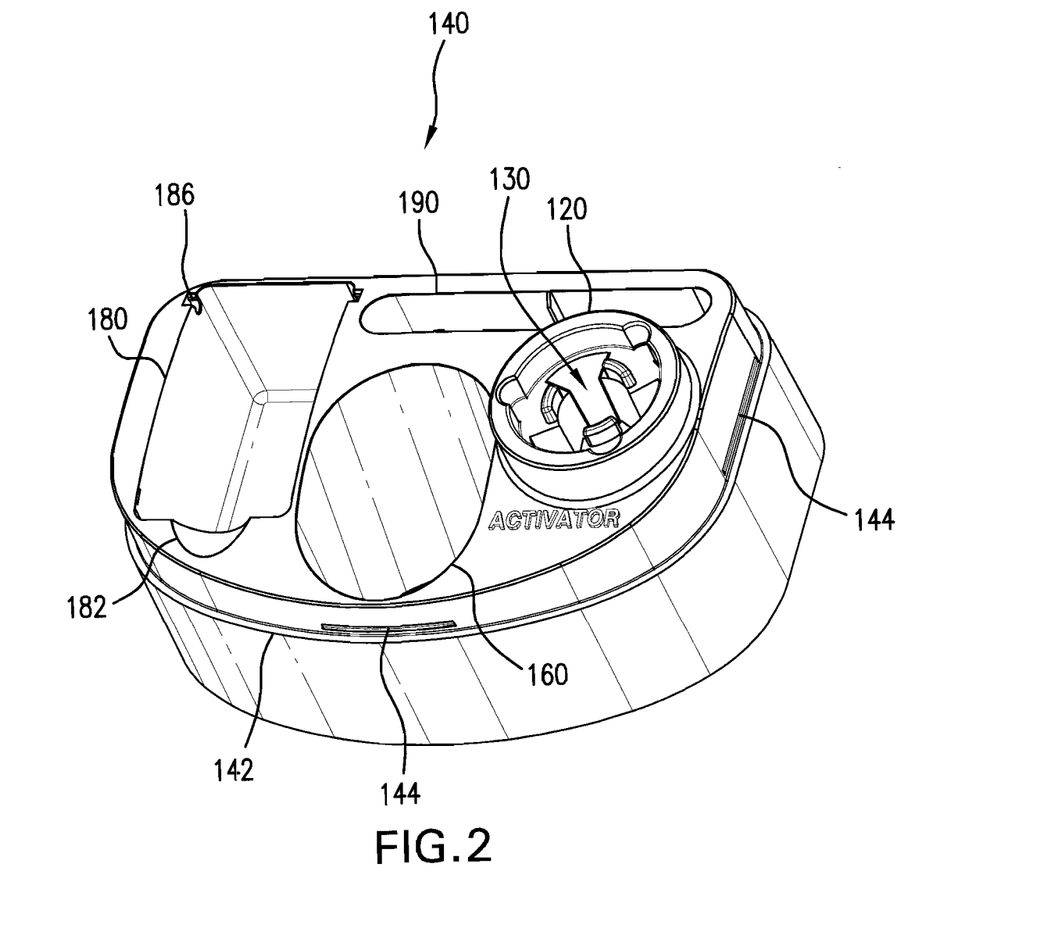
FIG. 2 is a perspective view of an example base of the example container shown in FIG. 1, according to an example embodiment of the present invention.

FIG. 2 is a perspective view of an embodiment of the base 140 of the container 100 according to FIG. 1. As an initial matter, it should be pointed out that in this figure and all proceeding figures, identical parts will be assigned the same reference numerals. In this embodiment, the valve actuation assembly 120 and/or the reservoir 130 may be formed integrally with the base 140. The base 140 may include a plurality of depressions for storing items belonging to or relating to the cryosurgery device. Specifically, the base 140 may contain a first depression 160 for storing the cryogen bottle 200. The first depression 160 may have an approximately frustoconical shape. In addition, the first depression 160 may have an approximately circular bottom 170 (see FIG. 3) and may be oriented in such a manner that when the cryogen bottle 200 is placed into the first depression 160, the cryogen bottle 200 is tilted back from a vertical position. Further with regard to FIG. 2, the base 140 may include a second depression 180, which may have approximately the shape of a rectangular prism and may be configured to store applicator tips 300 (see FIG. 11) for the cryosurgery device. The base 140 also includes a third depression 182, which may be arch-shaped and contiguous with the second depression 180. Furthermore, the base 140 may include a fourth depression 190, which may have the shape of an oblong slot and may be used, for example, to store an information booklet regarding the cryosurgery device. The base 140 may also include a shoulder 142, on which the cover 150 may rest, and ribs 144, which may aid in holding the cover in place. Typically, the base 140 may be injection-molded from one or more thermoplastic materials, such as polyethylene, polypropylene, or other polyolefins and polyolefin copolymers, nylons, polyesters, polyacetals, and polyurethanes. However, the base 140 may also be made of other suitable materials, such as styrenic resin polymers and copolymers, polyvinyl chloride, polyethylene terephthalate, polymethyl methacrylate and polycarbonate.

Figure 3:
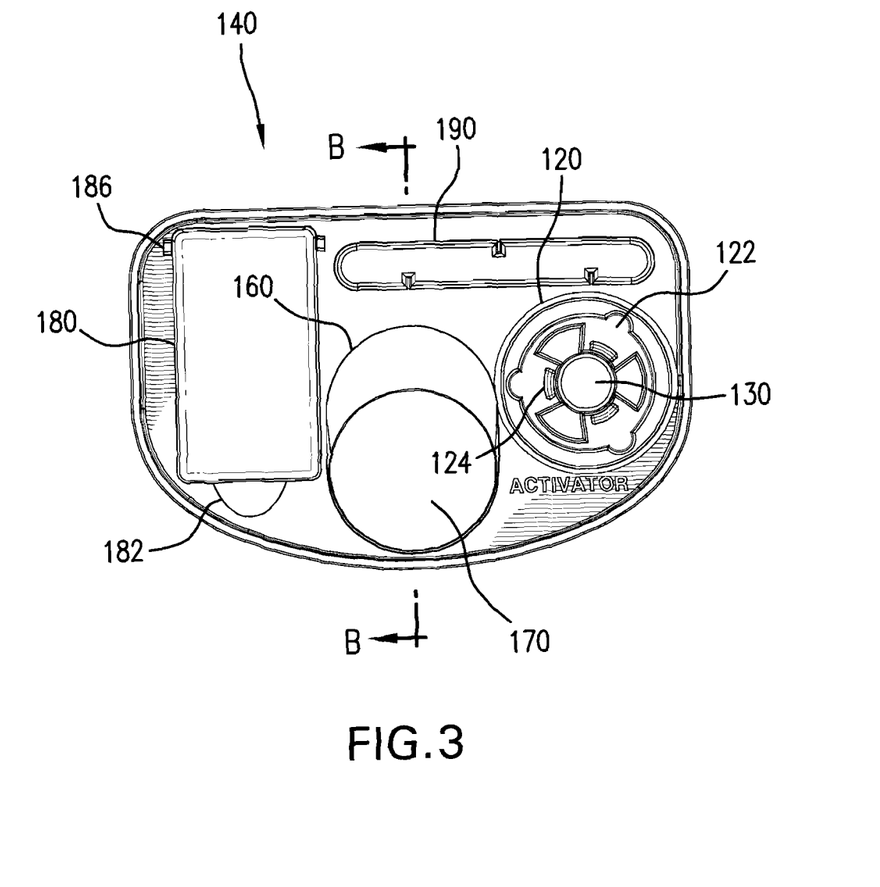
FIG. 3 is a top view of the example base of FIG. 2, according to an example embodiment of the present invention.
Figure 4:
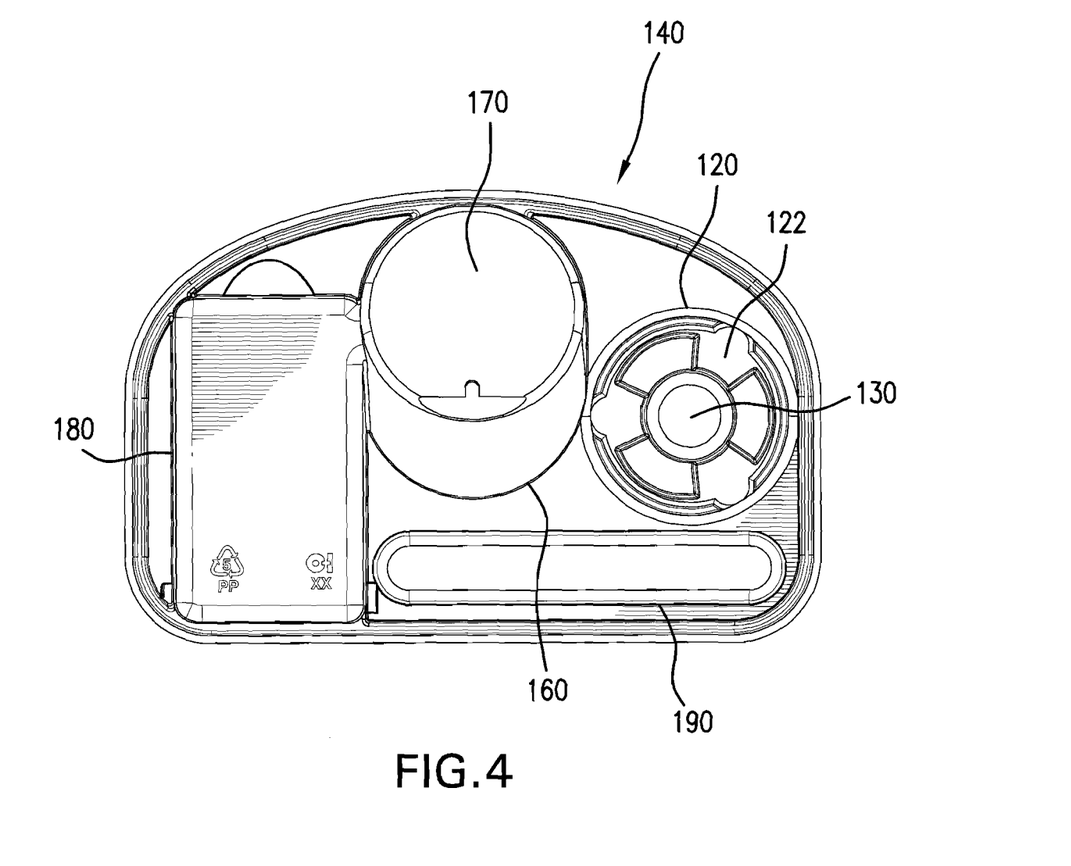
FIG. 4 is a bottom view of the example base of FIG. 2, according to an example embodiment of the present invention.

FIG. 3 is a top view of the base 140 of FIG. 2, according to an example embodiment of the present invention. From this view, it can be discerned that the bottom 170 of the frustoconical depression 160 is approximately circular in order for this depression 160 to receive a cylindrical cryogen bottle 200. In addition, it may also be discerned from this view that the reservoir 130 is approximately cylindrical in shape. Further with respect to FIG. 3, the valve actuation assembly 120 includes projections 122, upon which arcuate keys 124 are situated. These keys 124 may cooperate with the valve 230 in the cryogen bottle 200 to release refrigerant into the reservoir 130. FIG. 4 shows a corresponding bottom view of the base 140.

Figure 5:
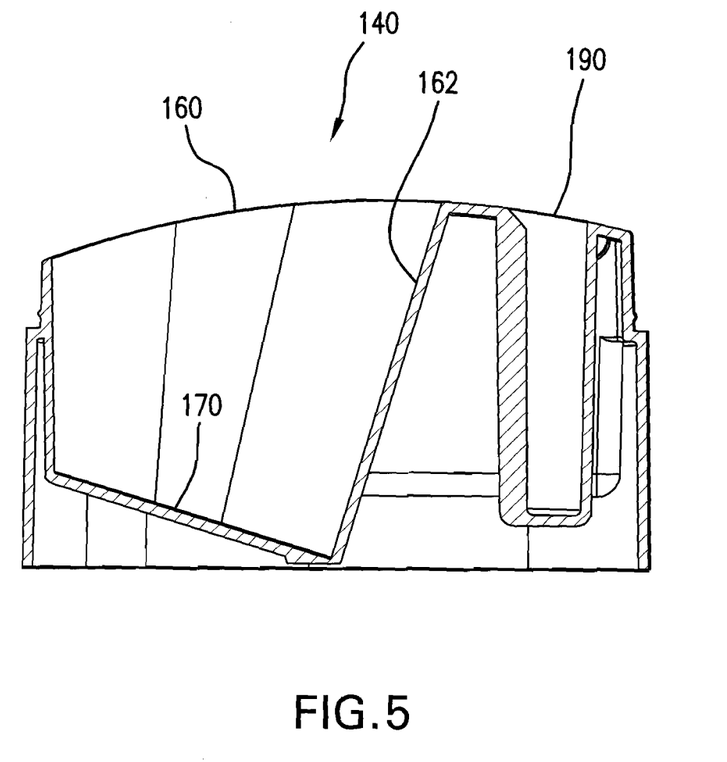
FIG. 5 is a representation of section B-B of the example base of FIG. 3, viewed in the direction of the arrows.

FIG. 5 is a sectional view of the example base of FIG. 3, along line segment B-B. As is apparent from this view, a sidewall 162 of the frustoconical depression 160 is oriented at an angle to a vertical direction, and the bottom 170 of the frustoconical depression 160 is oriented at an angle to a horizontal direction and approximately perpendicularly to the sidewall 162, so that the cylindrical cryogen bottle 200 supported in the depression 160 is tilted back at an angle to the vertical direction. This orientation of the cryogen bottle 200 may enable a consumer to more easily identify a brand label of the cryogen bottle 200 as the container 100 rests on a shelf in a store.

Figure 6:
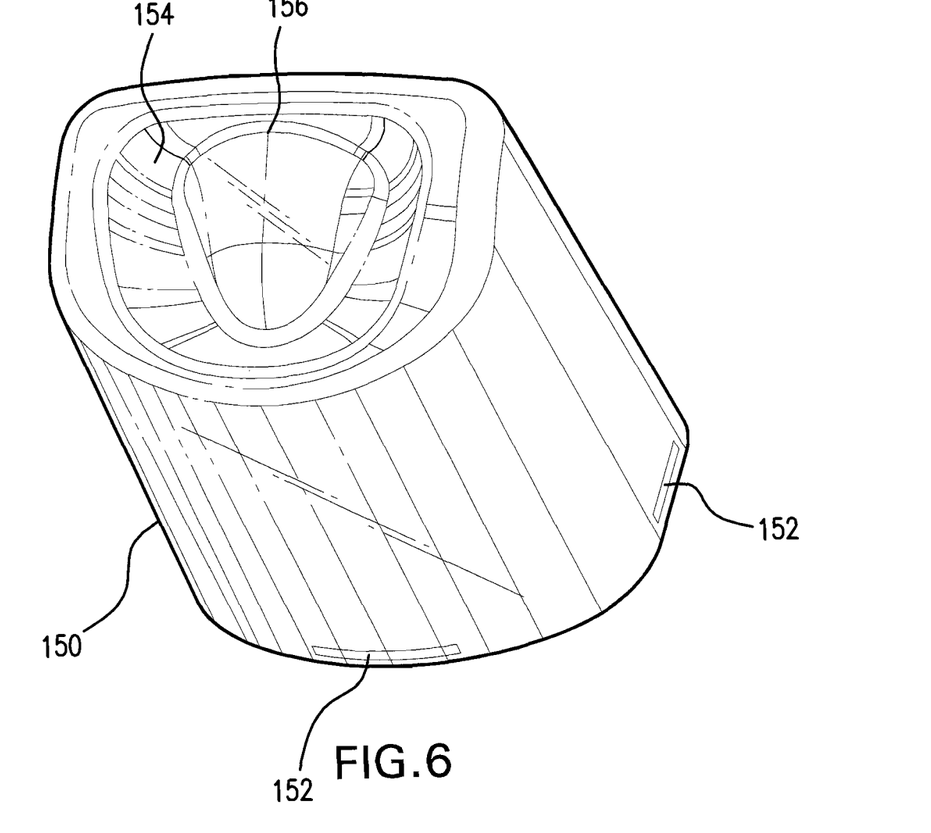
FIG. 6 is a perspective view of an example cover of the container of FIG. 1, according to an example embodiment of the present invention.

FIG. 6 is a perspective view of an example cover 150 of the container of FIG. 1. In this example embodiment, the cover 150 may be shaped approximately like a loaf of bread, i.e., having a cross section including two approximately parallel line segments joined on one side by a line segment approximately perpendicular to both, and joined on another side by an arcuate segment. However, the cover 150 may have any suitable shape, such as that of a cylinder, cone, pyramid, rectangular prism, etc. The cover 150 may be substantially transparent and may be made of materials, such as those mentioned above for the base 140, or other materials. The cover 150 may be slid onto the base 140 and come to rest on shoulder 142. In this embodiment, in order to effectively hold the cover 150 in place on shoulder 142, the cover may include ribs 152, which slide over and engage with the ribs 144 situated on the base 140. In addition, the ribs 152 and the ribs 144 may be continuous or intermittent. However, the cover 150 may be joined to the base 140 by other means, such as via hinges, latches, friction-fitting, etc. The cover 150 may additionally include a depression 154, out of which a protuberance 156 projects, or any other characteristic markings or designs.

Figure 7:
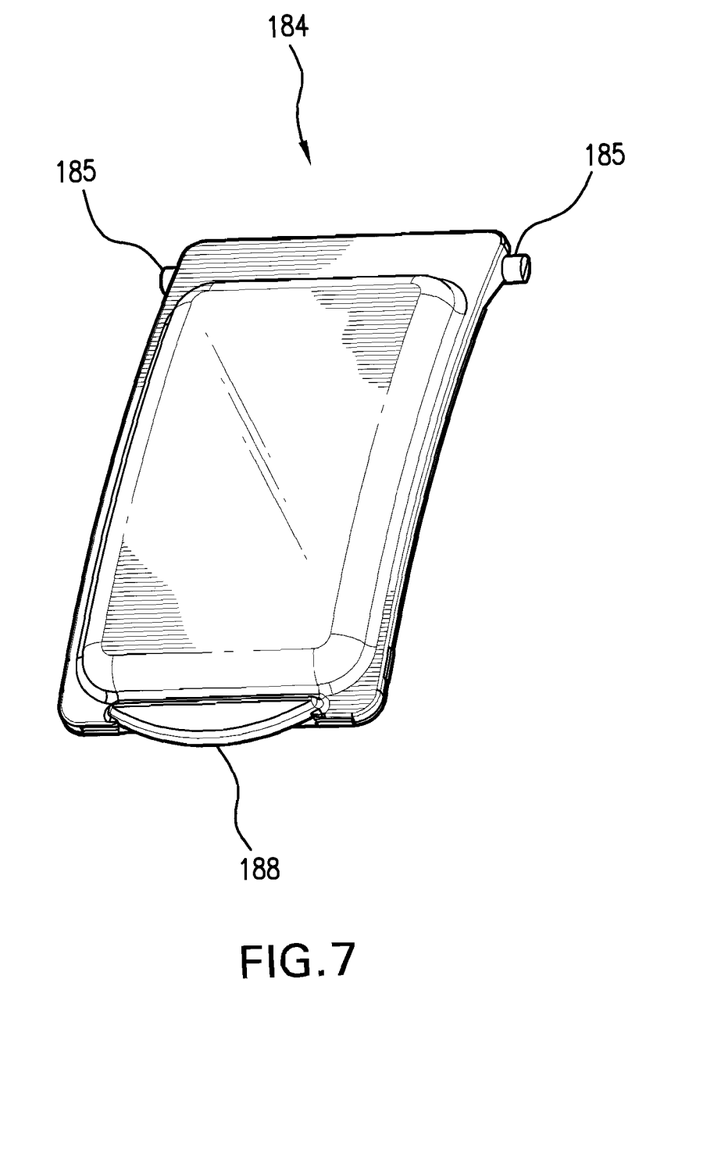
FIG. 7 is a perspective view of an example door for a depression in the base of FIG. 2, according to an example embodiment of the present invention.

FIG. 7 is a perspective view of an example door 184 for the second depression 180 in the base of FIG. 2. The door 184 may be configured to close off the second depression 180, thereby allowing any items stored in the second depression 180 to be separated from other portions of the base 140. The door 184 may be transparent and may have an approximately rectangular shape. In order to be able to attach the door 184 to the base 140 and pivot the door 184 with respect to the base 140, the door 184 may include cylindrical projections 185, which may be press-fit into recesses 186 on the base 140 and cooperate with these recesses 186 to form hinges. The door 184 may additionally include an arcuate lip 188. When the door 184 is in a closed position, the arcuate lip 188 may be situated over the depression 182 with a gap between the lip 188 and a base of the depression 182. In order to open the door 184, one must simply slide his or her finger into this gap and rotate the door 184 into an open position. In addition, the door may have side ribs and/or a front rib (not shown) configured to guide the door 184 into a proper seated position on the base 140, when the door 184 is closed. Furthermore, the lip 188 or any other part of the door 184 may include locking tabs (not shown) that engage with corresponding elements (not shown) situated on the base 140.

Figure 8:
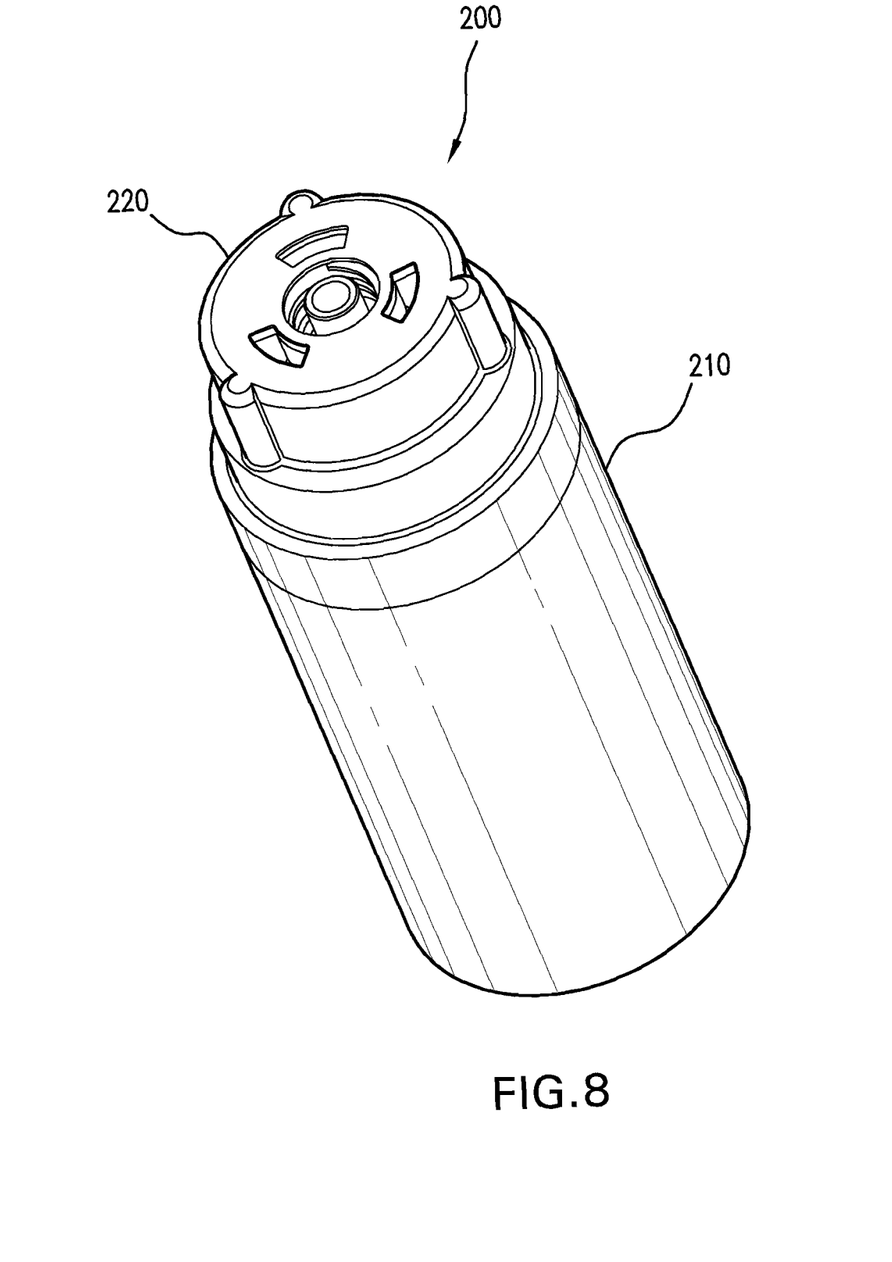
FIG. 8 is a perspective view of an example cryogen bottle according to an example embodiment of the present invention.

FIG. 8 is a perspective view of an example cryogen bottle 200, which is stored in the frustoconical depression 160 of the container 100 when not in use. The cryogen bottle 200 may include a cylindrical portion 210, in which liquid and/or gaseous refrigerant is stored, and a hub 220, which may be attached to the cylindrical portion in a manner known to one skilled in the art.

Figure 9:
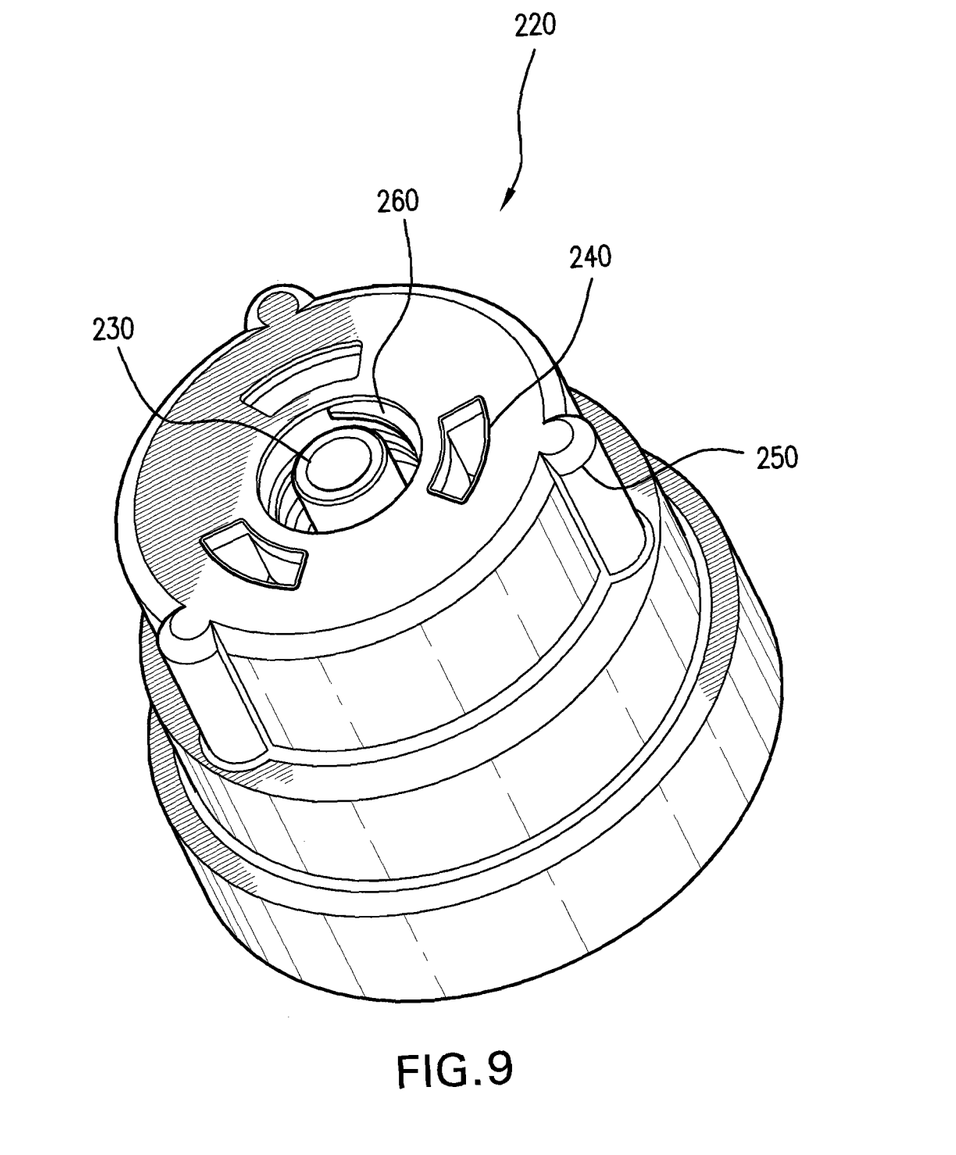
FIG. 9 is an enlarged perspective view of an example hub situated at the top of the cryogen bottle of FIG. 8, according to an example embodiment of the present invention.

FIG. 9 is an enlarged perspective view of the example hub 220 of FIG. 8. The hub 220 may include an aerosol valve 230 and slots 240, with which the arcuate keys 124 of the valve actuation assembly 120 may mate in order to actuate the aerosol valve 230. The aerosol valve 230 itself includes an annular actuating shoulder (not shown), which is situated inside the hub 220, directly beneath the slots 240. The hub 220 may further include aligning ribs 250, whose function will be explained with regard to FIG. 10. In addition, the hub 220 may include threads 260, which may engage with the applicator tip 300 (see FIGS. 11 and 13).

Figure 10:
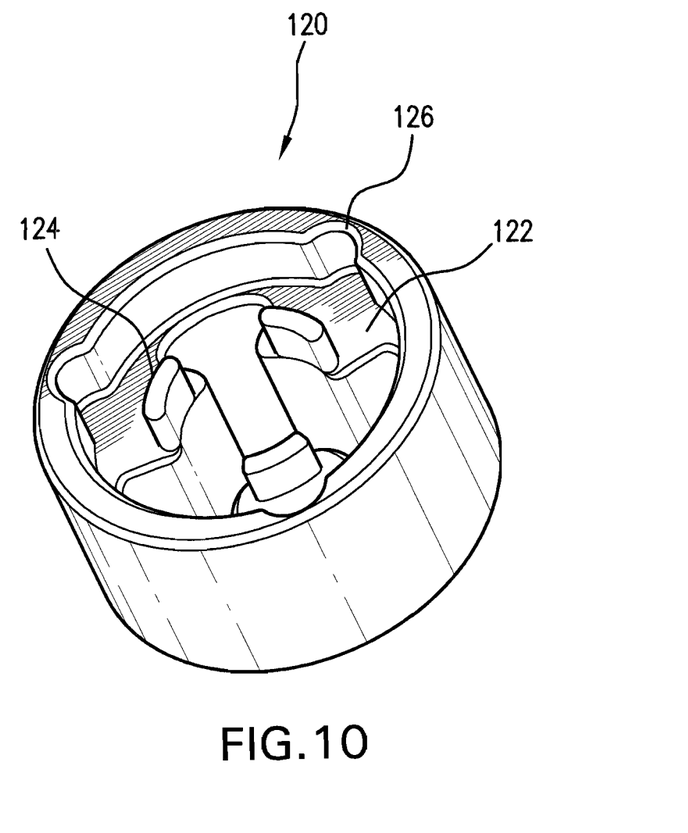
FIG. 10 is an enlarged perspective view of an example valve actuation assembly of the container of FIG. 1, according to an example embodiment of the present invention.

FIG. 10 is an enlarged perspective view of the example valve actuation assembly 120 of the container 100 shown in FIG. 1. As mentioned with regard to FIG. 3, the valve actuation assembly 120 includes projections 122, upon which arcuate keys 124 are situated. In addition, the valve actuation assembly 120 may include aligning recesses 126, with which the aligning ribs 250 of the hub 220 may mate in order to bring the slots 240 of the hub 220 in alignment with the arcuate keys 124. Furthermore, as is apparent from FIGS. 1 to 4 and 8 to 10, a width and depth of the base 140 are both substantially greater than a diameter of the valve actuation assembly 120 and a diameter of the cryogen bottle 200.

Figure 11:
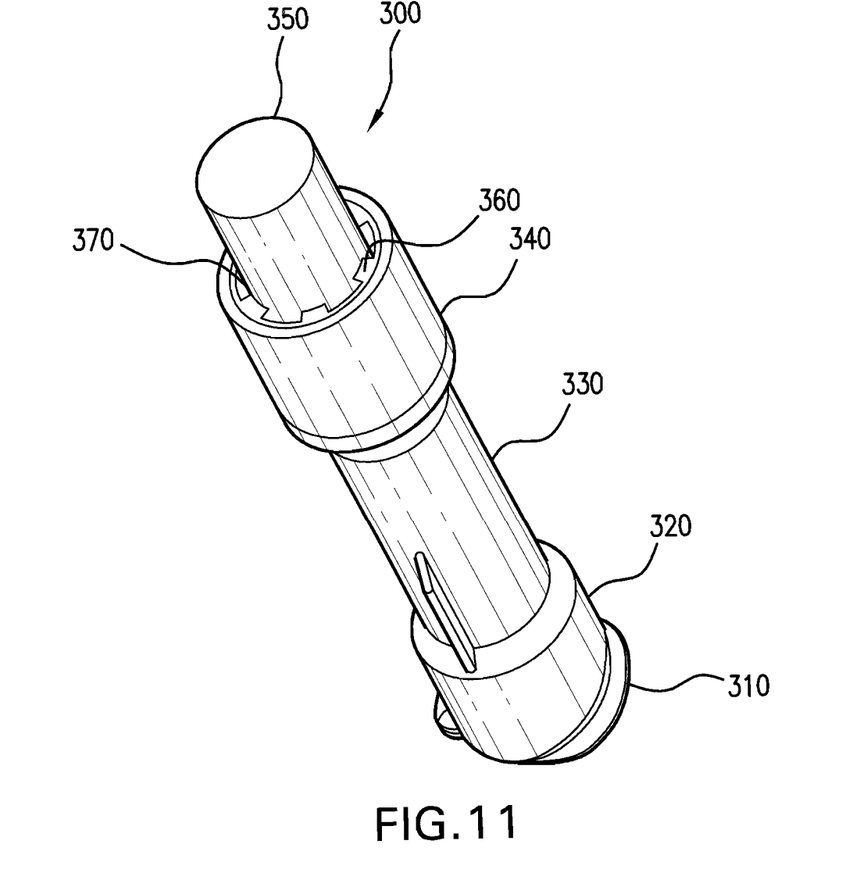
FIG. 11 is a perspective view of an example applicator tip that may be stored in the container of FIG. 1, according to an example embodiment of the present invention.
Figure 12:
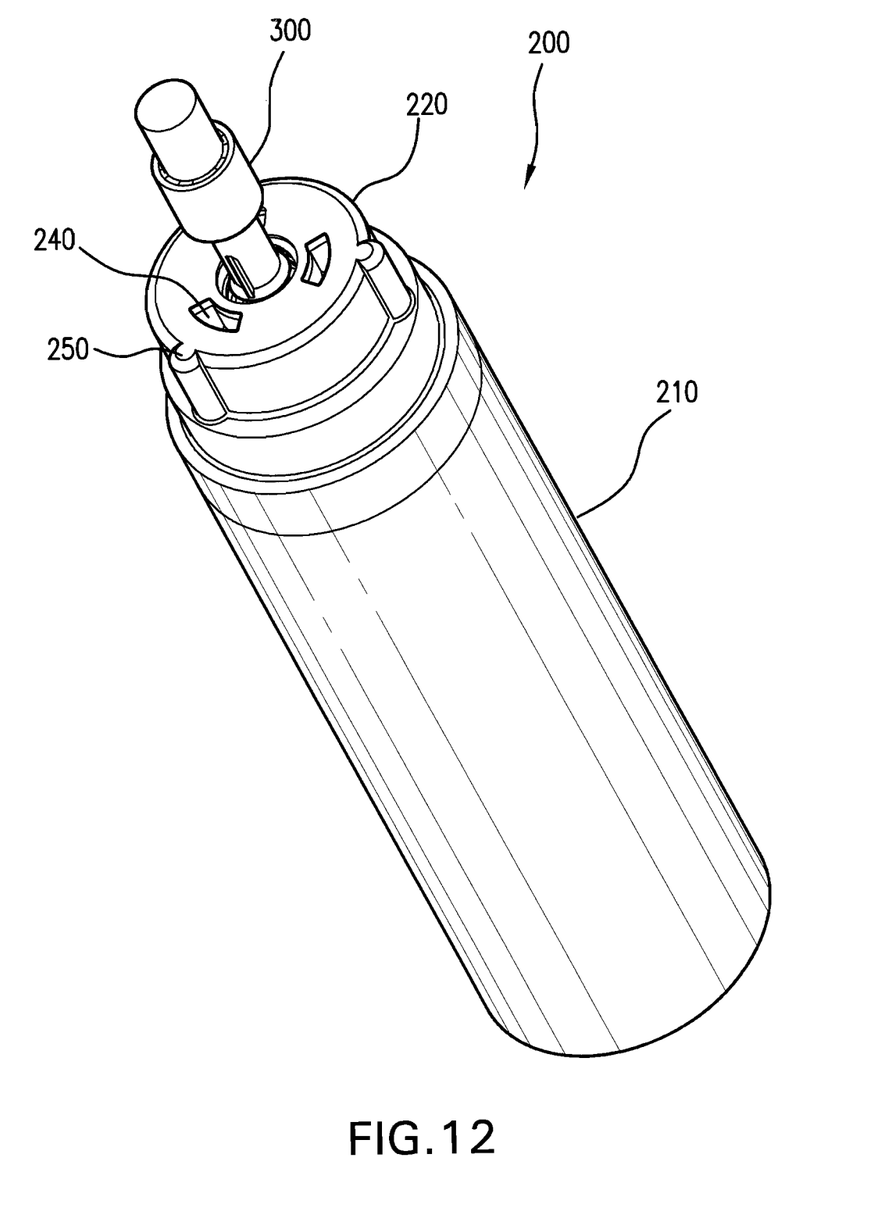
FIG. 12 is a perspective view of the example applicator tip of FIG. 11 attached to the cryogen bottle of FIG. 8, according to an example embodiment of the present invention.

FIG. 11 is a perspective view of an example applicator tip 300, a plurality of which may be stored in the container 100 of FIG. 1, in the depression 180, when the cryosurgery device is not in use. The applicator tip 300 is hollow and may have projections 310, which engage with the threads 260 of the hub 220 and allow the applicator tip 300 to be screwed onto the hub 220. FIG. 12 shows a perspective view of the cryogen bottle 200 with the applicator tip 300 screwed onto the hub 220. When the applicator tip 300 is screwed onto the hub 220, a lower section 320 of the applicator tip 300 mates with the aerosol valve 230, thereby forming a route for refrigerant to flow to the distal end of the applicator tip 300 upon actuation of the aerosol valve 230. The applicator tip 300 may also include a center section 330 and an upper section 340. A porous cylindrical tip 350 may be mounted in the upper section 340. In the mounted state, the cylindrical tip 350 stands flush against circumferentially spaced vertical projections 360. These projections 360 form circumferential grooves 370, through which refrigerant may flow upon actuation of the aerosol valve 230.

Figure 13:
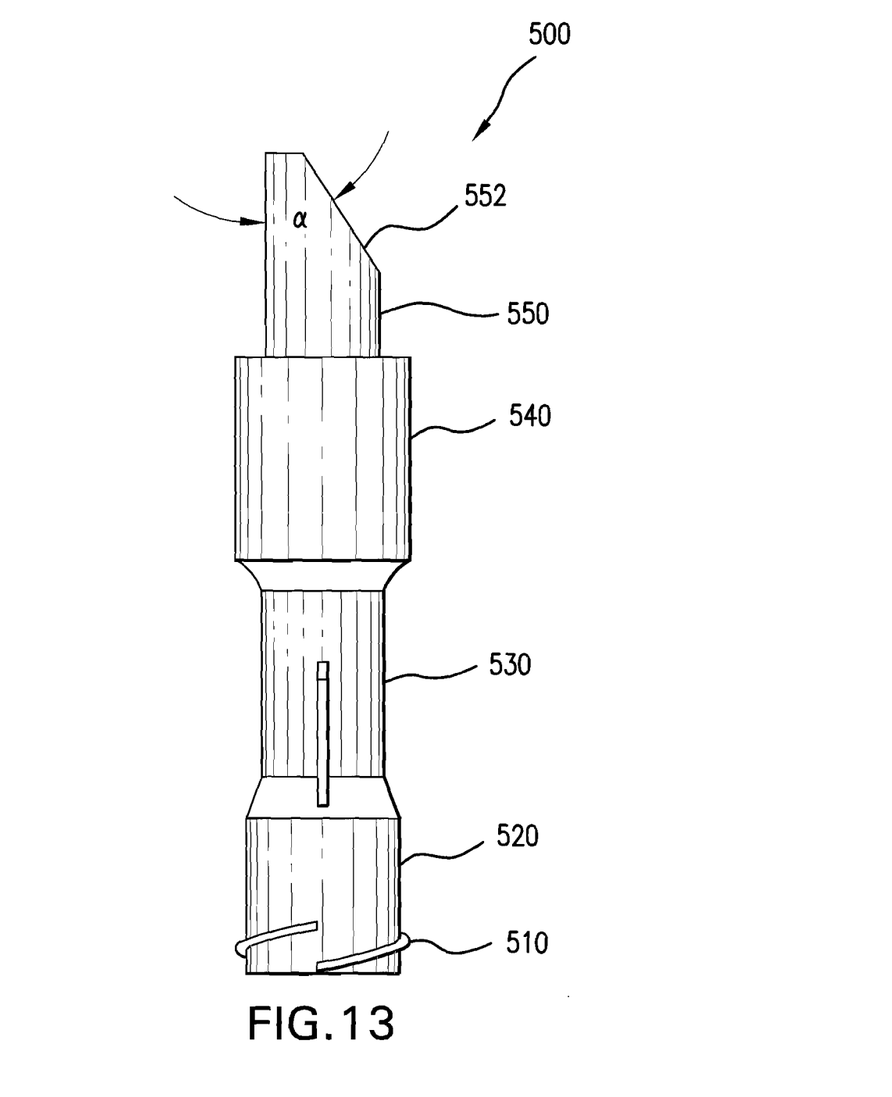
FIG. 13 is a front view of an alternative embodiment of an applicator tip according to the present invention.

FIG. 13 is a front view of an alternative embodiment of an applicator tip according to the present invention. Similarly to applicator tip 300, the alternative applicator tip 500 shown in FIG. 13 is hollow and includes projections 510, which may engage with the threads 260 of the hub 220 and allow the applicator tip 500 to be screwed onto the hub 220. When the applicator tip 500 is screwed onto the hub 220, a lower section 520 of the applicator tip 500 mates with the aerosol valve 230, thereby forming a route for refrigerant to flow to the distal end of the applicator tip 500 upon actuation of the aerosol valve 230. The applicator tip 500 may also include a center section 530 and an upper section 540. A porous, partially cylindrical tip 550 may be mounted in the upper section 540. In contrast to the cylindrical tip 350 of applicator tip 300, the partially cylindrical tip 550 of applicator tip includes a face 552 oriented at an angle α to an axial direction of the tip 550. The angle α is preferably 33° or less.

Figure 14:
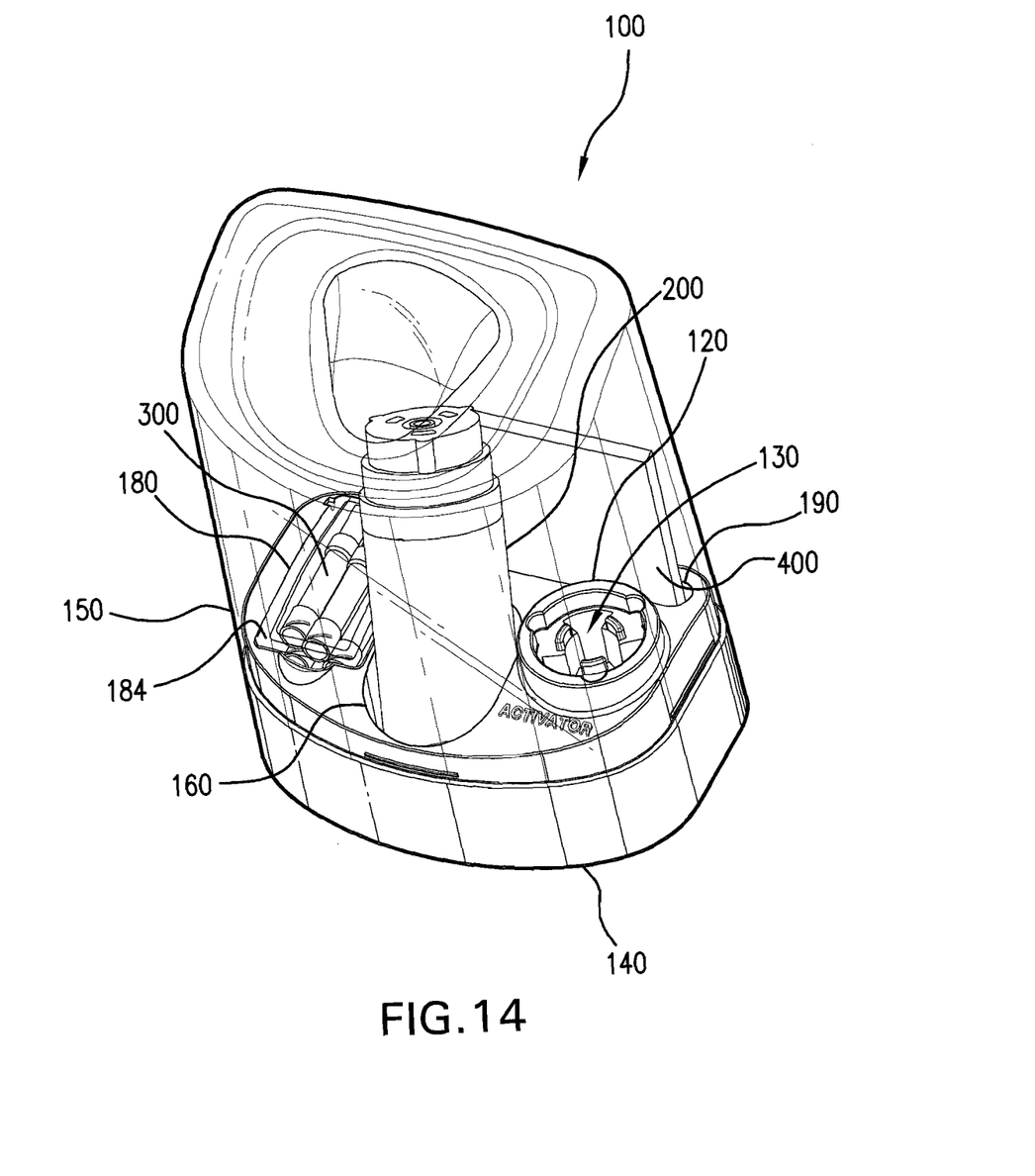
FIG. 14 is a perspective view of an example cryosurgery kit according to an example embodiment of the present invention.

FIG. 14 is a perspective view of an example cryosurgery kit according to an example embodiment of the present invention. The cryosurgery kit may include the container 100, which itself may include the base 140 and the cover 150. The cryosurgery kit may also include the cryogen bottle 160, a plurality of applicator tips 300, the valve actuation assembly 120, the reservoir 130, the door 184, and an information booklet 400. The cryogen bottle 200 is situated in the depression 160 such that the cryogen bottle 200 is tilted back from a vertical position. Applicator tips 300 may be stored in the second depression 180. The door 184 may aid in keeping the applicator tips 300 from inadvertently spilling out of the second depression 180 and may prevent excess dirt, dust, moisture or other foreign material from settling on the applicator tips 300. One applicator tip 300 may also be pre-attached to the hub 220 of the cryogen bottle 200, in order to show proper assembly. The information booklet 400 may be stored in the fourth depression 190. In addition, a card (not shown) including a brand name, picture, diagram or other product information, including treatment instructions and recommendations, may be inserted or mounted in the fourth depression 190.

The cryosurgery device stored in container 100 may be used, for example, to treat warts, skin tags and other skin lesions. In operation of this device, the cryogen bottle 200 is removed from the frustoconical depression 160 of base 140 and placed in an upright position. An applicator tip 300 is then removed from the second depression 180 in the base 140 and screwed onto the hub 220 of the cryogen bottle 200 via threads 260. The cryogen bottle/applicator tip assembly is then turned upside down and caused to mate with the valve actuation assembly 120. In so doing, the cryogen bottle 200 is rotated until the aligning ribs 250 of the hub 220 are in alignment with, and engage with, the aligning recesses 126 of the valve actuation assembly 120. The arcuate keys 124 of the valve actuation assembly 120 and the slots 240 of the hub 220 are positioned relative to the aligning recesses 126 and the aligning ribs 250, respectively, in such a manner, that the arcuate keys 124 engage with the slots 240 simultaneously to the aligning ribs 250 engaging with the aligning recesses 126. A downward force is then applied by hand to the cryogen bottle 200 for a time period of, for example, approximately 2 to 3 seconds. As mentioned with regard to FIG. 10, the width and depth of the base 140 are substantially greater than the diameter of the valve actuation assembly and the diameter of the cryogen bottle 200, which may allow the base 140 to remain stable and not tip as the downward force is applied to the valve actuation assembly 120. During application of the force, the arcuate keys 124 press down on the annular shoulder of the valve 230, situated directly beneath the slots 240, and actuate the valve 230. As a result, the valve 230 is opened and refrigerant from the cryogen bottle 200 enters the applicator tip 300 and travels through the lower and center sections 320, 330 of the applicator tip 300. When the refrigerant reaches the upper section 340 of the applicator tip 300, the refrigerant is channeled through grooves 370 onto the porous cylindrical tip 350 and into the reservoir 130. As the refrigerant flows onto the cylindrical tip 350, the tip 350 is cooled to a temperature of approximately $-20°$ C. or less. The force is then removed from the cryogen bottle 200, thereby causing the aerosol valve 230 to close and the flow of refrigerant to cease. The cryogen bottle/applicator tip assembly is then removed from the valve actuation assembly 120, and the applicator tip 300 is applied to a wart, skin tag or other skin lesion for an appropriate period of time.

The above-mentioned container 100 having base 140 with depressions for storage and a valve actuation assembly 120 for operation has several advantages. First of all, the parts of the cryosurgery device are stored in one place. In addition, the valve actuation assembly 120 and reservoir 130 are connected to and/or integrated into a stable base 140 that will remain steady even when a non-vertical force component is introduced into the cryogen bottle 200 during actuation of aerosol valve 230. Furthermore, the reservoir 130 ensures that the refrigerant expelled from the cryogen bottle 200 is retained near the porous cylindrical tip 350 of the applicator tip 300, efficiently utilized and not inadvertently spilled.

In an alternative embodiment of the cryosurgery device, no applicator tip 300 needs to be screwed onto the hub 220 of the cryogen bottle 200. Instead, refrigerant from the cryogen bottle 200 may simply be injected directly into the reservoir, and a swab may be subsequently immersed in a resulting pool of refrigerant in the reservoir 130. In certain embodiments, the swab may be an applicator tip 300 that has not been chilled by refrigerant as described above, but is manually inserted into reservoir disconnected from the cryogen bottle 200 After a prescribed period of time, the swab may be removed from the reservoir and applied to a wart, skin tag or other skin lesion.

The foregoing description discloses only exemplary embodiments of the invention. Modification of the above-disclosed apparatus which falls within the scope of the invention will be readily apparent to those of ordinary skill in the art. Accordingly, while the present invention has been disclosed in connection with exemplary embodiments thereof, it should be understood that other embodiments may fall within the spirit and scope of the invention, as defined by the following claims.

What is claimed is:

1. A container for a cryosurgery device which includes a cryogen bottle, comprising:
a container body including an internal space configured to hold the cryogen bottle; a valve actuation assembly mechanically coupled to the container body, the valve actuation assembly configured to actuate a valve on the cryogen bottle; a reservoir positioned relative to the valve actuation assembly so that the reservoir receives refrigerant from the cryogen bottle when the valve on the cryogen bottle is actuated using the valve actuation assembly; a base, wherein the valve actuation assembly and the reservoir are integral parts of the base; and a cover configured to form a closed volume with the base, the closed volume dimensioned large enough to contain the cryogen bottle.

2. The container of claim 1, wherein the reservoir is situated beneath the valve actuation assembly.

3. The container of claim 1, wherein a width and a depth of the base are substantially greater than a diameter of the cryogen bottle and a diameter of the valve actuating assembly.

4. The container of claim 1, wherein the base includes a first depression into which the cryogen bottle may be placed.

5. The container of claim 4, wherein the first depression is approximately frustoconical.

6. The container of claim 5, wherein the first depression has an approximately circular bottom and is oriented such that when the cryogen bottle is placed in the first depression, the cryogen bottle is tilted back from a vertical position.

7. The container of claim 1, wherein the base includes a second depression configured to receive applicator tubes for the cryogen bottle.

8. The container of claim 7, wherein the second depression has approximately a shape of a rectangular prism.

9. The container of claim 8, wherein the base includes a door that closes off the second depression when the door is in a closed position.

10. The container of claim 8, wherein the base includes a third depression contiguous with the second depression.

11. The container of claim 10, wherein the third depression has approximately a shape of an arch.

12. The container of claim 1, wherein the cover is substantially transparent.

13. The container of claim 1, wherein the base includes a fourth depression having a shape of an oblong slot.

14. A cryosurgery kit, comprising:
a cryogen bottle; a container holding the cryogen bottle; and a valve actuation assembly mechanically coupled to the container, the valve actuation assembly configured to actuate a valve on the cryogen bottle, and a base, wherein the valve actuation assembly is an integral part of the base and the base includes a frustoconical-shaped depression, a rectangular-prism shaped depression having a substantially transparent door, and a slot-shaped depression.

15. The cryosurgery kit of claim 14, wherein the cryogen bottle is situated in the frustoconical-shaped depression.

16. The cryosurgery kit of claim 14, further comprising:
a plurality of applicator tips situated in the rectangular-shaped depression; and an information booklet situated in the slot-shaped depression.

17. A container for a cryosurgery kit, comprising:
a base means configured for holding a plurality of kit components; an activator means for activating a cryogen bottle, the activator means formed as an integral component of the container; and a reservoir means for receiving refrigerant from the cryogen bottle when the cryogen bottle is activated by the activator means and a transparent cover means for forming a closed volume with the base means, the closed volume containing the plurality of kit components.

18. A container for a cryosurgery device which includes a cryogen bottle, comprising:
a container body including an internal space sufficiently large to hold the cryogen bottle;
a valve actuation assembly mechanically coupled to the container body, the valve actuation assembly configured to actuate a valve on the cryogen bottle;
a reservoir positioned relative to the valve actuation assembly so that the reservoir receives refrigerant from the cryogen bottle when the valve on the cryogen bottle is actuated using the valve actuation assembly;
a base, wherein the valve actuation assembly and the reservoir are integral parts of the base; and
a cover configured to form a closed volume with the base, the closed volume dimensioned large enough to contain the cryogen bottle;
wherein the reservoir is situated beneath the valve actuation assembly; the base includes a first depression into which the cryogen bottle may be placed; the first depression is approximately frustoconical; the first depression has an approximately circular bottom and is oriented such that when the cryogen bottle is placed in the first depression, the cryogen bottle is tilted back from a vertical position; the base includes a second depression in which applicator tubes may be stored; the second depression has approximately a shape of a rectangular prism; the base includes a door that closes off the second depression when the door is in a closed position; the cover is substantially transparent; the base includes a third depression contiguous with the second depression; the third depression has approximately a shape of an arch; and the base includes a fourth depression having a shape of an oblong slot.

19. A cryosurgery kit, comprising:
a cryogen bottle; a container holding the cryogen bottle; a valve actuation assembly mechanically coupled to the container, the valve actuation assembly configured to actuate a valve on the cryogen bottle; a liquid storage reservoir coupled to the container, the reservoir positioned relative to the valve actuation assembly so that the reservoir receives refrigerant from the cryogen bottle when the valve on the cryogen bottle is actuated using the valve actuation assembly; a transparent cover coupled to the base; a plurality of applicator tips; and an information booklet; wherein the container further comprises a base; the valve actuation assembly is an integral part of the base; the reservoir is an integral part of the base; the base includes a frustoconical-shaped depression, a rectangular-prism shaped depression having a substantially transparent door, and a slot-shaped depression; the cryogen bottle is situated in the frustoconical-shaped depression; the plurality of applicator tips are situated in the rectangular-shaped depression; and the information booklet is situated in the slot-shaped depression.

* * * * *